(12) United States Patent
Ma

(10) Patent No.: US 11,040,144 B1
(45) Date of Patent: Jun. 22, 2021

(54) PLUNGER ASSEMBLY FOR A SYRINGE APPARATUS

(71) Applicant: Shao Ma, Taylor, MI (US)

(72) Inventor: Shao Ma, Taylor, MI (US)

( * ) Notice: Subject to any disclaimer, the term of this patent is extended or adjusted under 35 U.S.C. 154(b) by 143 days.

(21) Appl. No.: 15/703,299

(22) Filed: Sep. 13, 2017

(51) Int. Cl.
*A61M 5/24* (2006.01)
*A61M 5/32* (2006.01)
*A61M 5/31* (2006.01)

(52) U.S. Cl.
CPC ............ *A61M 5/3129* (2013.01); *A61M 5/24* (2013.01); *A61M 5/3148* (2013.01); *A61M 5/32* (2013.01); *A61M 2005/2403* (2013.01)

(58) Field of Classification Search
CPC ............... A61M 5/3129; A61M 5/445; A61M 2005/3209; A61M 2005/3131; A61M 2005/3132; A61M 5/24; A61M 5/3213; A61M 5/321
See application file for complete search history.

(56) References Cited

U.S. PATENT DOCUMENTS

| | | | | |
|---|---|---|---|---|
| 4,632,672 A | * | 12/1986 | Kvitrud | A61B 5/150236 604/222 |
| 4,772,273 A | * | 9/1988 | Alchas | A61J 1/05 604/218 |
| 5,779,668 A | * | 7/1998 | Grabenkort | A61M 5/3129 604/191 |
| 8,469,923 B2 | * | 6/2013 | Vedrine | A61M 5/284 604/414 |
| 2001/0004700 A1 | * | 6/2001 | Honeycutt | A61B 17/320758 606/159 |
| 2004/0153038 A1 | * | 8/2004 | Guala | A61M 39/14 604/263 |
| 2005/0165360 A1 | * | 7/2005 | Stamp | A61M 5/2033 604/187 |
| 2005/0238297 A1 | * | 10/2005 | Saitoh | G02B 6/4292 385/94 |
| 2008/0183122 A1 | * | 7/2008 | Fisher | G01N 21/31 604/21 |
| 2008/0275397 A1 | * | 11/2008 | Bonnette | A61M 39/04 604/117 |
| 2011/0213311 A1 | * | 9/2011 | Xu | A61M 5/31511 604/187 |

* cited by examiner

*Primary Examiner* — Manuel A Mendez
*Assistant Examiner* — Justin L Zamory

(57) ABSTRACT

A plunger assembly (200) for use in a syringe apparatus (100). The plunger assembly (200) includes a movable tip (280) that can be removably secured to a plunger rod (210). By positioning the movable tip (280) in a barrel (300) while air (70) can still pass through a hole (282) in the movable tip (280), a user (90) can use the plunger assembly (200) to easily remove air (70) from a syringe apparatus (100) that has been loaded with the desired liquid (80).

12 Claims, 15 Drawing Sheets

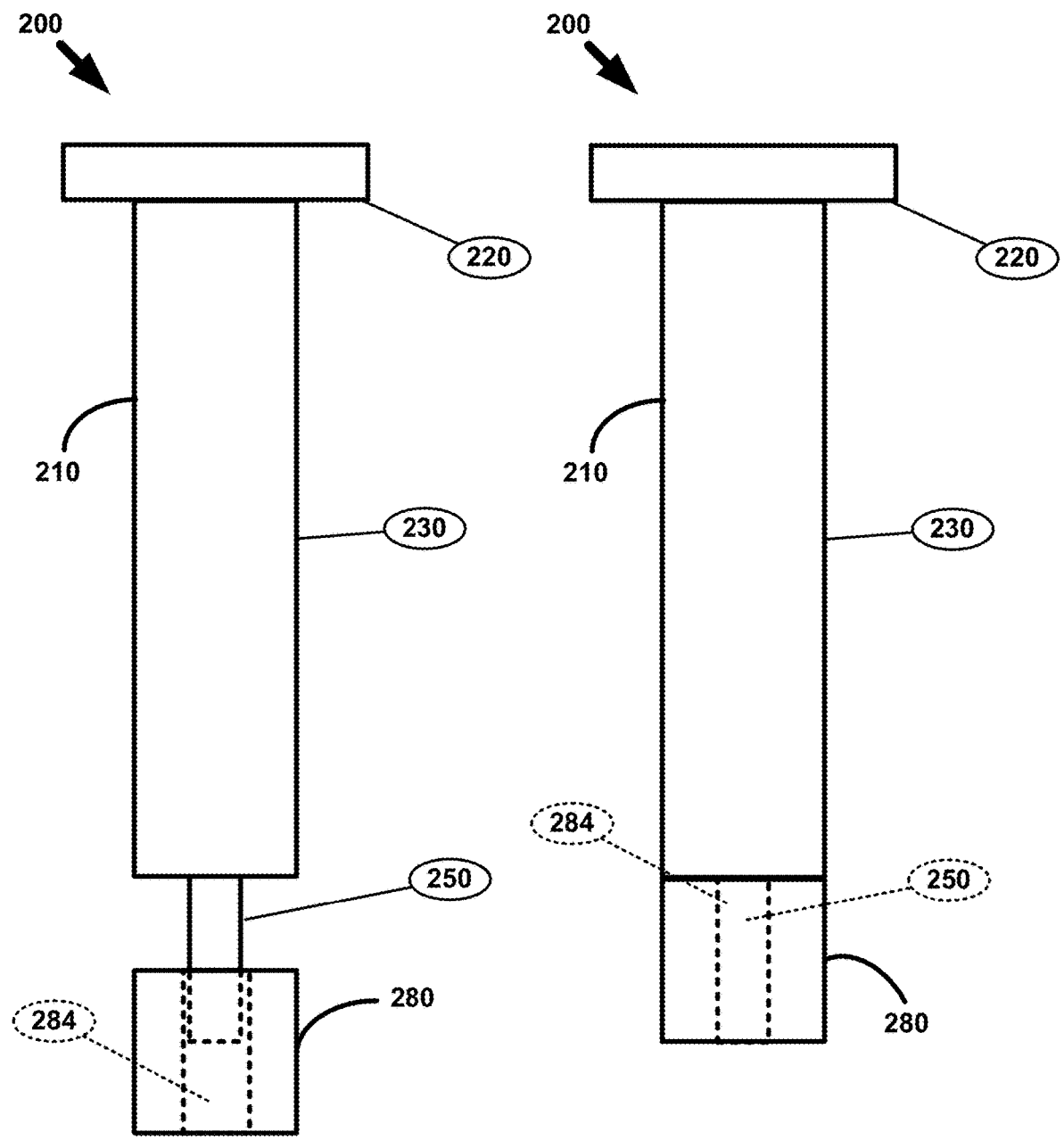
FIGURE 2D  FIGURE 2E

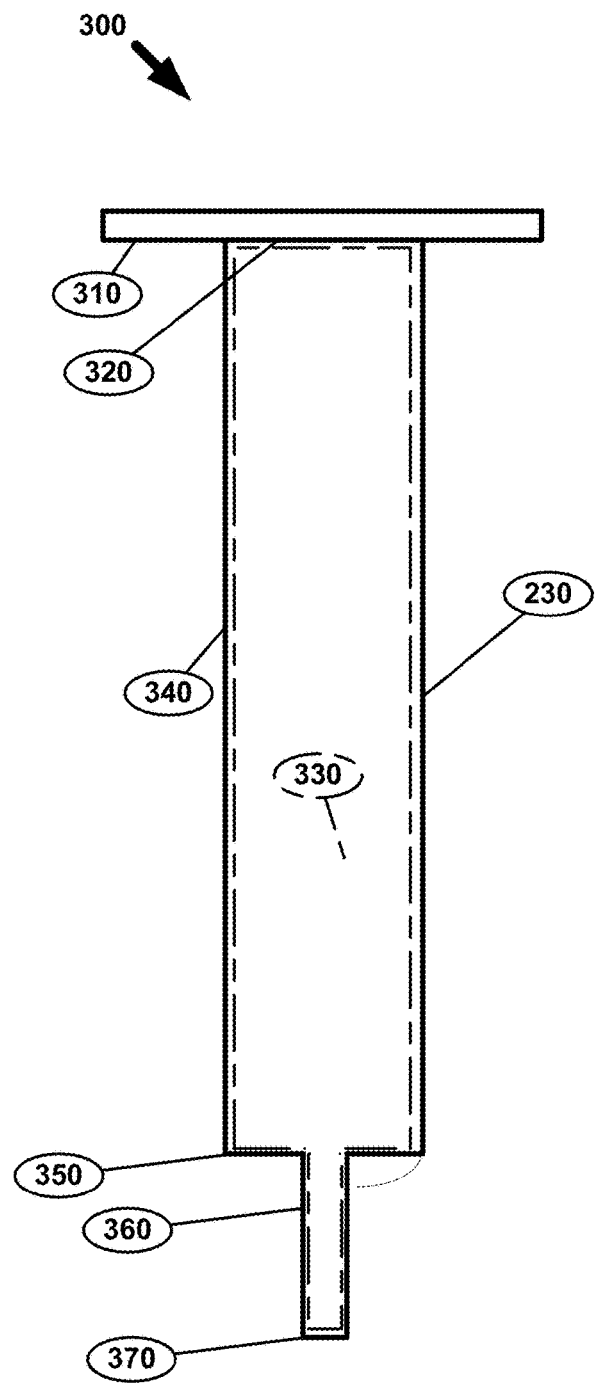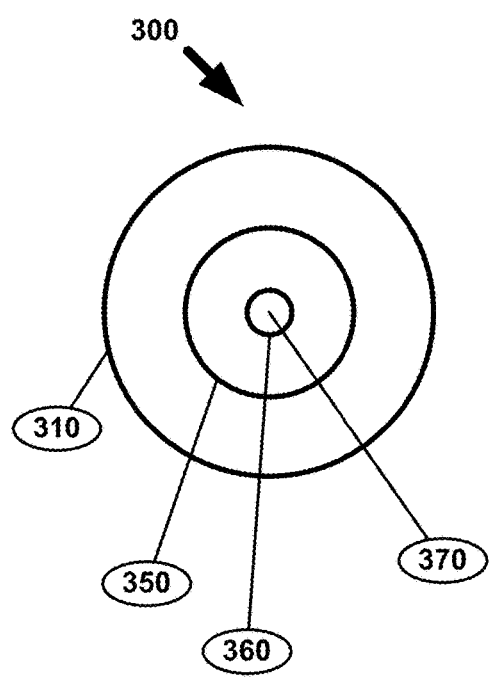
FIGURE 3A
FIGURE 3B

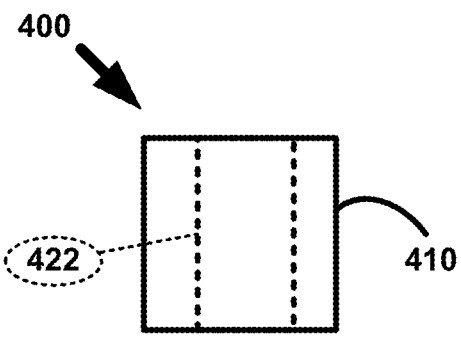
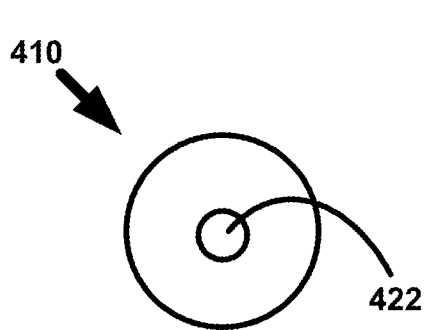
FIGURE 4B
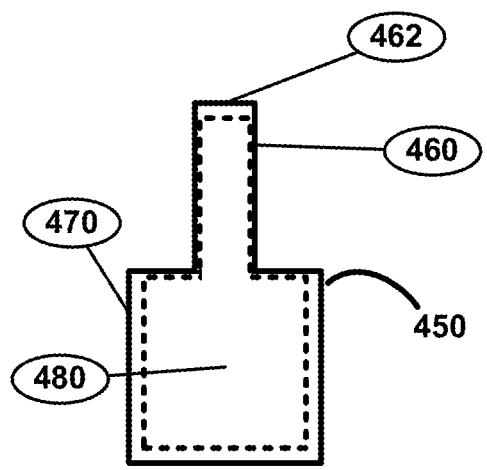
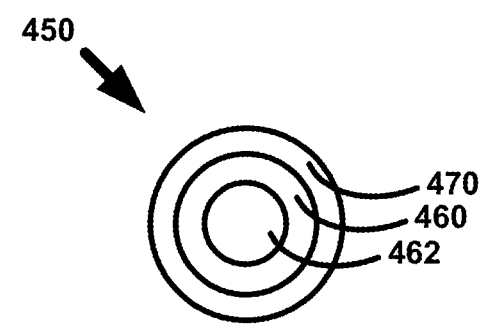
FIGURE 4C
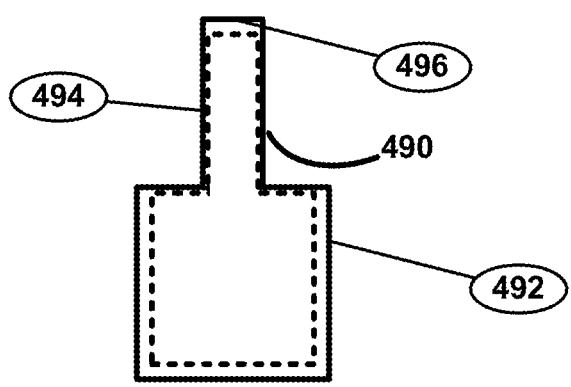
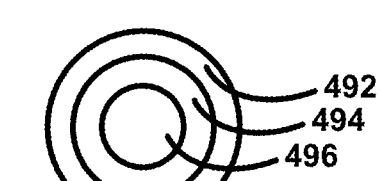
FIGURE 4D
FIGURE 4A

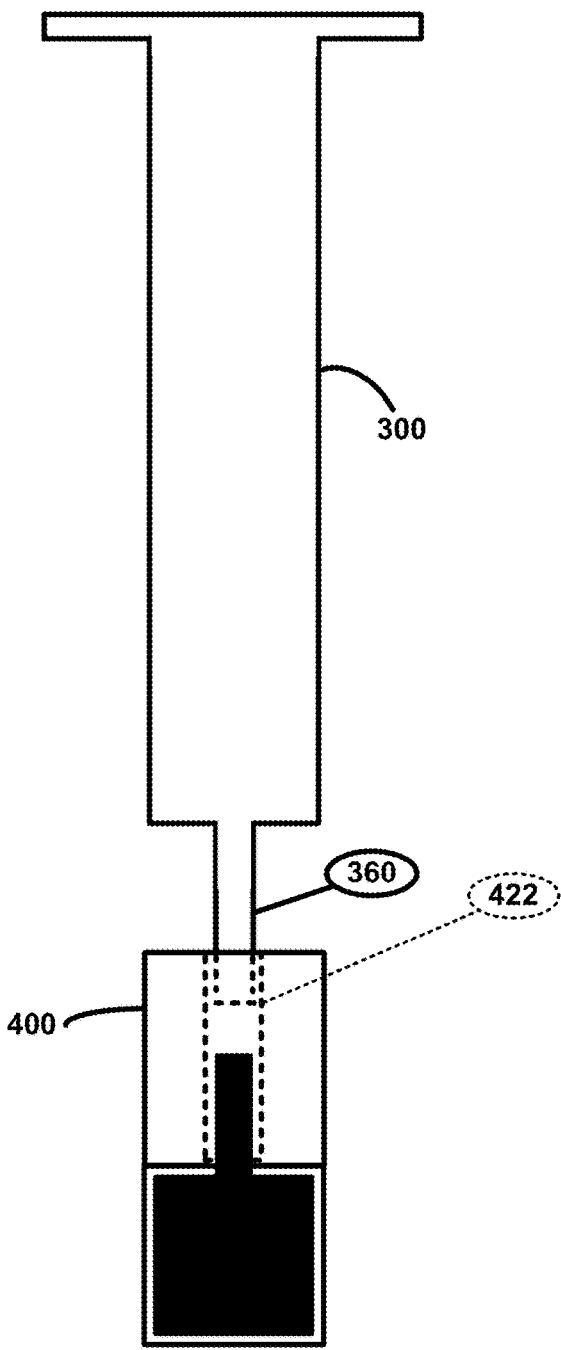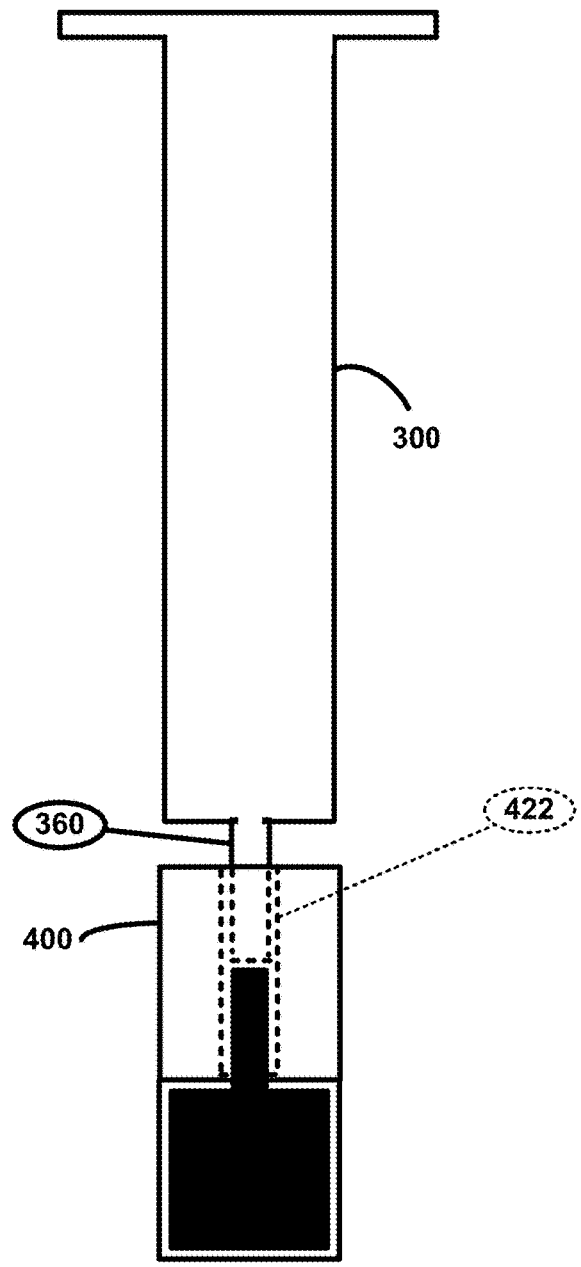
FIGURE 5A  FIGURE 5B

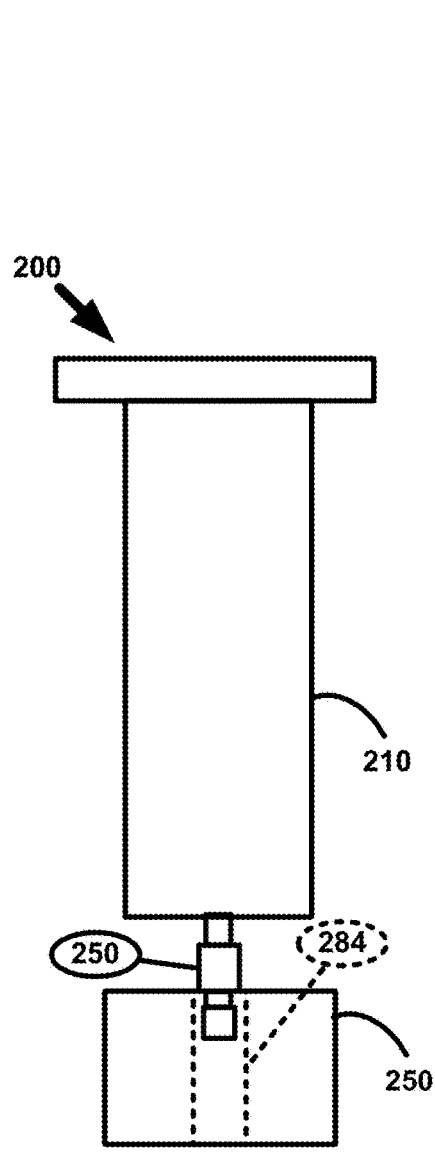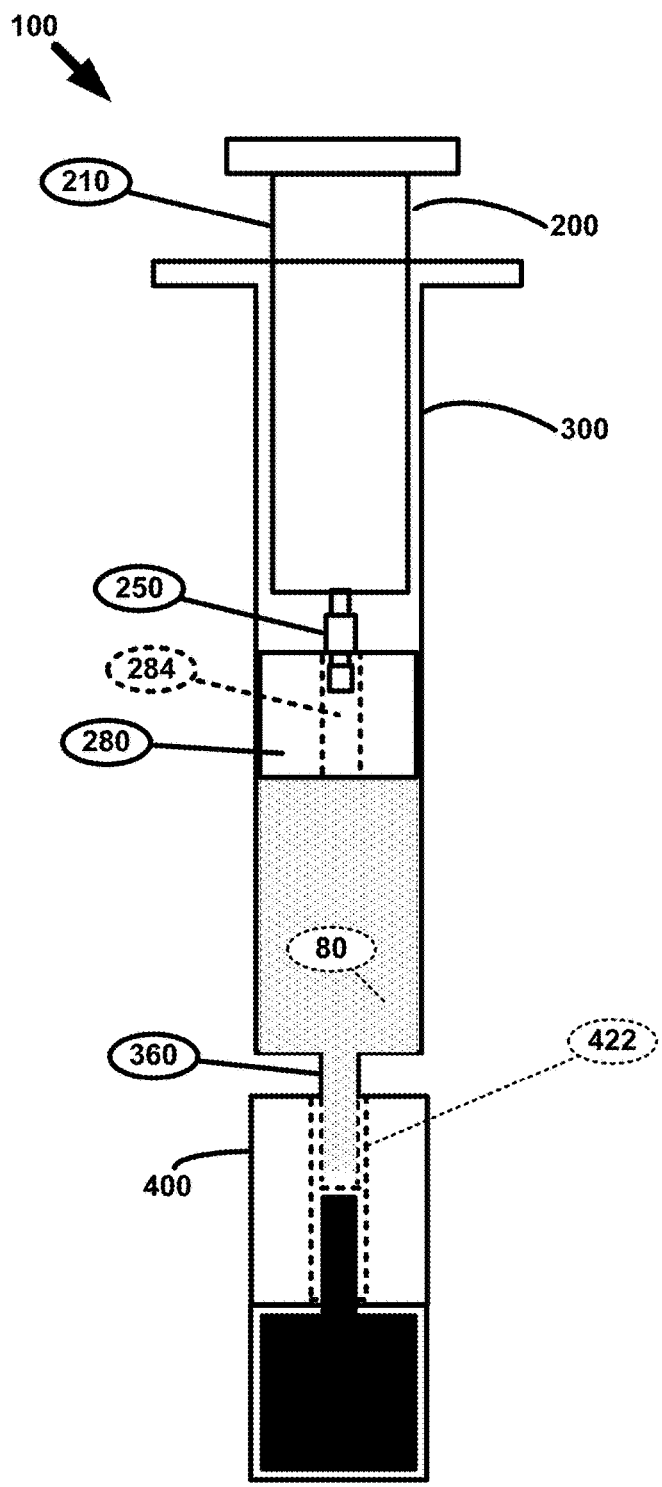
FIGURE 5E
FIGURE 5F

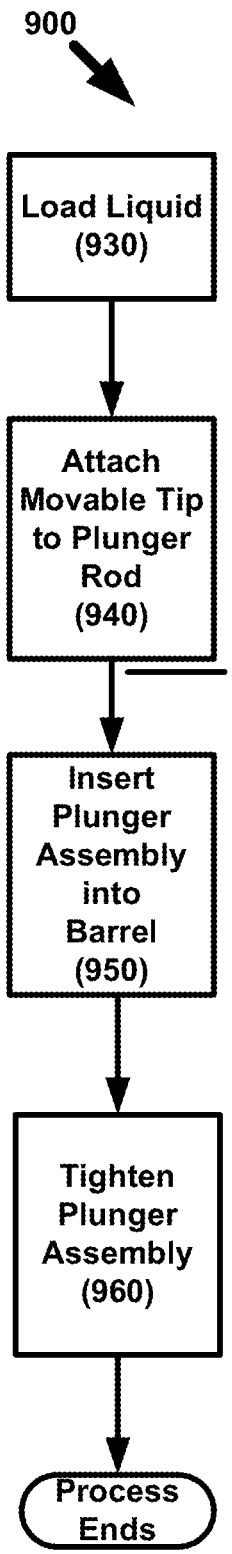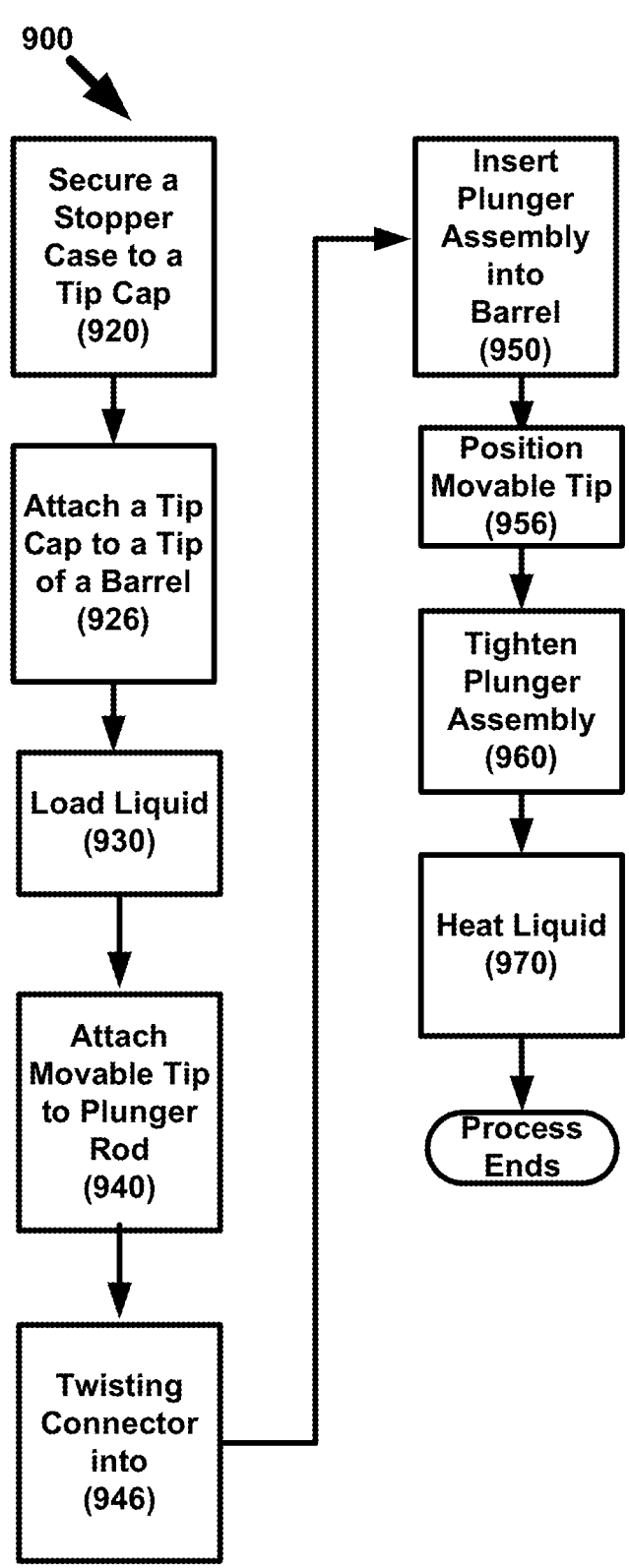
FIGURE 6A
FIGURE 6B

PLUNGER ASSEMBLY FOR A SYRINGE APPARATUS

BACKGROUND OF THE INVENTION

The invention relates generally to syringes. More specifically, the invention relates to a plunger assembly for use in a syringe apparatus and a corresponding method of use (collectively, the "apparatus").

Syringes are used for a variety of different purposes. Syringes are loaded with liquids that are stored until they are dispersed. A wide variety of liquids can be utilized in conjunction with a syringe, including a variety of oils, medicines, or even water.

SUMMARY OF THE INVENTION

The invention relates generally to syringes. More specifically, the invention relates to a plunger assembly for use in a syringe apparatus and a corresponding method of use (collectively, the "apparatus").

The apparatus includes a plunger assembly, a barrel, and a stopper assembly. The plunger assembly can be implemented as two parts that can be securely combined together and subsequently removed. By using a plunger assembly that includes a movable tip that can be removably attached to a connector on the bottom of the plunger rod, the user of the apparatus can force air out of the internal cavity of the barrel by twisting the plunger rod into the movable tip. Air is pushed out of a hole, such as an axial hole, in the movable tip. The removal of air from the internal cavity of the barrel can eliminate undesirable oxidation to the liquid as well as undesirable bubbles of air when the liquid contents are disbursed from the apparatus.

Additional components such as a battery and heating elements can be included in the plunger assembly to enable to user of the apparatus to heat the liquid in the apparatus. In some such embodiments, heat conductive wires can be included in the sides of the barrel used to hold the liquid.

BRIEF DESCRIPTION OF THE DRAWINGS

Different examples of various components, attributes, compositions, and processes can be incorporated into the making of the plunger assembly and other aspects of the apparatus. Some of those variations are illustrated in the drawings described briefly below. However, no patent application can expressly disclose in words or in drawings, all of the potential embodiments of an invention. In accordance with the provisions of the patent statutes, the principles, compositions, and processes relating to the plunger assembly and apparatus are illustrated in certain preferred embodiments. However, it must be understood that the apparatus and method of using the apparatus may be practiced otherwise than is specifically illustrated without departing from its spirit or scope.

FIG. 2D is a side view diagram illustrating an example of a plunger assembly in an upright, attached, but not fully secured state, with the connector being partially inside the axial hole of the movable tip.

FIG. 2E is a side view diagram illustrating an example of a plunger assembly in an upright, attached, and fully secured state, with the connector being securely positioned through the axial hole of the movable tip.

FIG. 3A is a side view diagram illustrating an example of a barrel in an upright position.

FIG. 3B is a bottom view diagram illustrating an example of a barrel.

FIG. 4A is a side view diagram illustrating an example of a stopper assembly in an upright but disassembled state.

FIG. 4B is a top view diagram illustrating an example of a tip cap.

FIG. 4C is a top view diagram illustrating an example of a stopper case.

FIG. 4D is a top view diagram illustrating an example of a stopper.

FIG. 5A is a side view diagram illustrating an example of a stopper assembly being attached but not fully secured to the tip of a barrel.

FIG. 5B is a side view diagram illustrating an example of a stopper assembly that is fully attached and secured to the tip of a barrel.

FIG. 5E is a side view diagram illustrating an example of an assembled plunger assembly where the movable tip is not fully tightened to the plunger rod.

FIG. 5F is a side view diagram illustrating an example of the plunger assembly of FIG. 5E being inserted into the barrel and stopper assembly of FIG. 5C. The movable tip has been pushed down to the point where liquid occupies the barrel. The movable tip has still not been fully tightened with respect to the plunger rod.

FIG. 6A is a flow chart diagram illustrating an example of using the plunger assembly in utilizing a syringe.

FIG. 6B is a flow chart diagram illustrating an example of using the plunger assembly in utilizing a syringe.

DETAILED DESCRIPTION

The invention relates generally to syringes. More specifically, the invention relates to a plunger assembly for use in a syringe apparatus and a corresponding method of use (collectively, the "apparatus").

I. Overview and Introduction of Elements

Figure 1A:
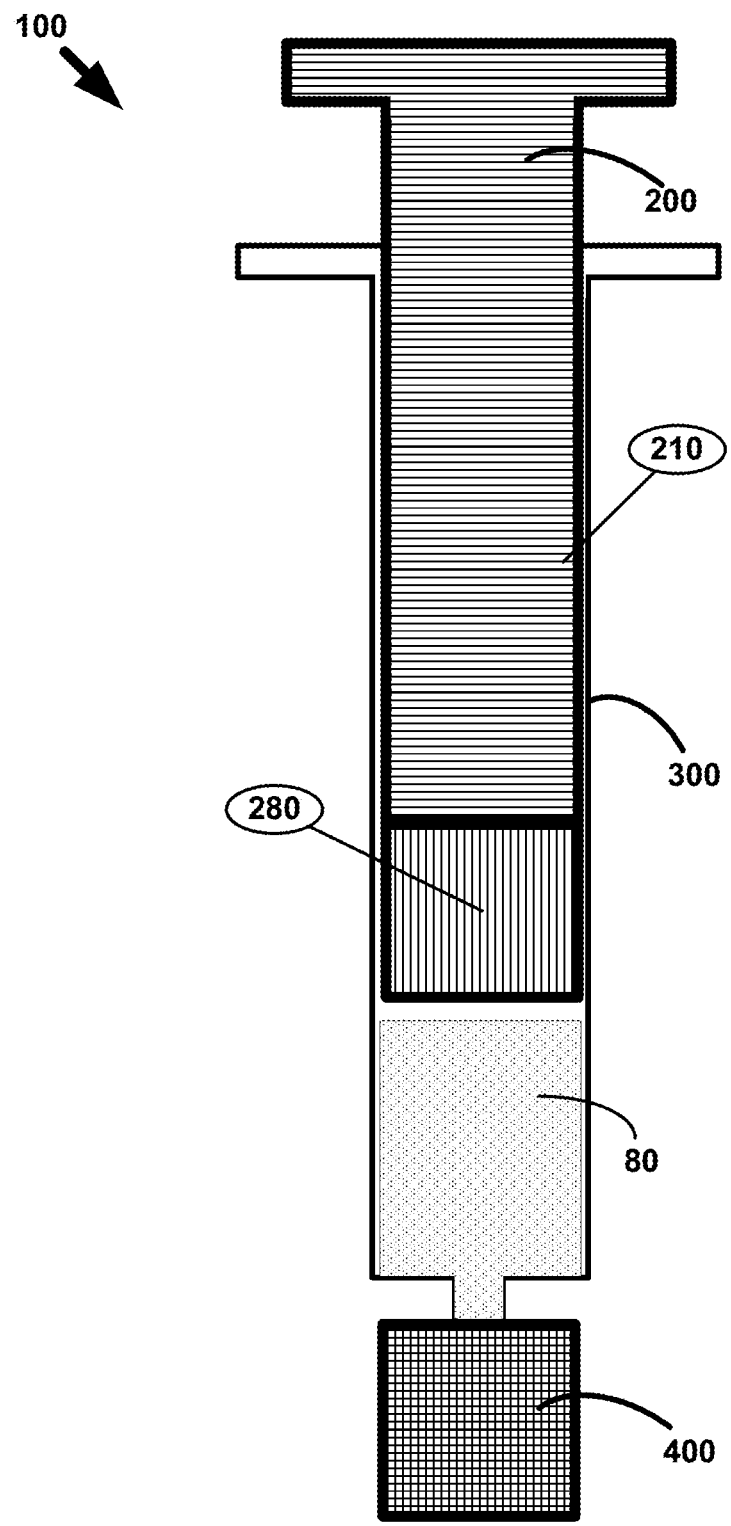
FIG. 1A is a side view diagram illustrating an example of an apparatus in an upright position that has been loaded with liquid, where the movable tip has been tightened to the plunger rod.

All terms and element numbers referenced below or in the Figures are included in an index of claim terms set forth in Table 1 below. As illustrated in FIG. 1A, a syringe apparatus 100 can include a plunger assembly 200, a barrel 300, and a stopper assembly 400. The various assemblies are illustrated separately from each other in FIG. 1B (plunger assembly 200), FIG. 1C (barrel 300), and FIG. 1D (stopper assembly 400).

A. Plunger Assembly

The two main components of plunger assembly are typically the plunger rod 210 and a movable tip 280, as illustrated in FIGS. 1A, 1B, 2A, 2D, and 2E. As illustrated in those Figures and as set forth in Table 1, the plunger assembly can include a plunger rod 210, a tab 220 for pressing down the plunger rod 210, a main body 230, a heat source 240, a battery 242, a button 246, a USB port, a connector 250, one or more threads 252 on the connector 250, one or more o-rings 254 on the connector 250, a movable tip 280, a hole 282 such as an axial hole 284 in the movable tip 280, one or more o-rings 266 on the exterior surface of the movable tip 280, a bottom surface 290 on the movable tip 280, and one or more heating elements 292 on either the movable tip and/or plunging rod 210.

Different embodiments of the plunger assembly 200 can have different numbers of these components. Some embodiments of the plunging assembly 200 will be quite basic, including only the core of a movable tip 280 that is capable of being removably attached and secured to the plunging rod 210.

The function of the plunger assembly 200 is to provide a user 90 with the means to remove air 70 from the cavity 330 of the barrel 300 after liquid 80 has been loaded into the cavity 330. The configuration of a movable tip 280 that is capable of being loosened and tightened on a connector 250 of the plunging rod 210 can enable a user 90 to remove air 70 from the cavity 330 by pushing it through a hole 282, such as an axial hole 284, in the movable tip 280 as the plunger rod 210 is screwed more tightly into the movable tip 280. In some embodiments of the apparatus 100, the plunger assembly can also be used to heat the liquid 80 while the liquid 80 is stored in the cavity 330 of the barrel 300. This can be done using a battery and one or more heating elements 292 in the plunger assembly 200.

The plunger assembly 200 can also be used to discharge the liquid 80 stored in the barrel 300, consistent in the manner that a prior art plunger would perform such a function.

B. Barrel

As illustrated in FIGS. 1A, 1C, 3A, and 3B, and as referenced in Table 1, a barrel 300 can include a lip 310, a mouth 320, an internal cavity 330 for holding a liquid 80, a main body 340, a base 350, a tip 360, an opening 370, and one or more wires 380 to transmit heat from the battery 242 of the plunger assembly 200. With the exception of heating embodiment of the apparatus 100 that includes one or more wires 380 for the purposes of heating the liquid 80, the barrel 300 of the apparatus 100 is consistent with the barrel 300 of the prior art.

C. Stopper Assembly

A barrel 300 includes a cavity 330 into which a liquid 80 is loaded. A stopper assembly 400, which can be comprised of a single integral stopper 490 or a configuration of components that include a stopper prevent the liquid 80 from flowing out of an opening 370 in the tip 360 when the stopper assembly 400 is secured onto the tip 360. The apparatus can be implemented in a variety of different configurations using a variety of different components. The apparatus 100 can use a wide variety of different stoppers and stopper assemblies as known in the prior art.

II. Innovative Functions

The apparatus 100 can be used to achieve one or both of the following functions/advantages:

A. Removal of Air from a Cavity of a Barrel

When a liquid 80 is loaded into the cavity 330 of the barrel 300, some of the air 70 within the cavity 330 is displaced, but some air 70 nonetheless remains. The movable tip 280 has a hole 282, typically an axial hole 284, that allows air 70 to pass through the movable tip 280, which in turn allows it to be easily positioned just above the liquid 80. By positioning the bottom surface 290 of a movable tip 280 on the "high water line" of the liquid 80, the user can then screw the connector 250 of the plunger rod 210 deeper into the axial hole 284 of the movable tip 280 until the plunger assembly is fully secure and the air 70 within the cavity 330 has been removed.

Removal of the air 70 from the cavity 330 can prevent oxidation of the liquid 80 (depending on what is being stored) as well as prevent air bubbles from being discharged from the cavity 330 when the liquid 80 is discharged from the cavity 330.

Various threaded surfaces, o-rings, and other attributes can be incorporated into the movable tip 280 and the plunger rod 210 to maximize the ability of those components to be moved with respect to each other and with respect to the barrel 330. Such attributes can also be used to facilitate a secure mating between the movable tip 280 and the plunger rod 210.

B. Heating of the Liquid

Some embodiments of the plunger assembly 200 can provide users 90 with the ability to heat the liquid 80 using components included in the apparatus 100 itself. The apparatus 100 can utilize a heat source 240 such as battery 242 can be used to deliver electricity. A user control such as a button 246 can be used to activate or deactivate the heating of the liquid 80. A USB port 248 can provide users 90 with the opportunity to recharge the battery 242. Heating elements 292 can be located in the movable tip and/or the plunger tip 210. It may also be desirable in certain embodiments of the apparatus 100 for the barrel 300 to include wires 380 along the sides to promote the transmission of heat from the heat source 240 to the liquid 80 in the cavity 330.

III. Alternative Embodiments

The innovative plunger assembly 200 was originally conceived to facilitate the movement of air 70 outside the cavity 330 of the barrel 300. The core structure that enable that functionality is a plunger assembly 200 in which a movable tip 280 can be removably attached/secured/unsecured/unattached from the plunger rod 210. With a hole 282 to allow for the movement of air 70 through the movable tip 280, the movable tip 280 can be placed on the "high water line" of the liquid 80, and the plunger rod 210 can then be screwed into otherwise moved into the hole 280 in the movable tip 280.

This core structure can be implemented in conjunction with a wide variety of different embodiments of the apparatus 100. Different embodiments of the plunger assembly 200, barrel 300, and stopper assembly 400 can implement this core innovative function.

To facilitate the movement, mating, and unmating of the movable tip 280 to the plunger rod 210, attributes such as o-rings, threaded surfaces, dimensional shapes, etc can be used. There are a wide variety of such supportive feature designs that can be incorporated into the apparatus 100.

Similarly, there are a variety of different battery 242, heating element 292, and other heat-related component configurations that can be incorporated into the apparatus 100.

Different examples of various components, attributes, compositions, and processes can be incorporated into the making of the plunger assembly and other aspects of the apparatus. Some of those variations are illustrated in the drawings described briefly below. However, no patent application can expressly disclose in words or in drawings, all of the potential embodiments of an invention. In accordance with the provisions of the patent statutes, the principles, compositions, and processes relating to the plunger assembly and apparatus are illustrated in certain preferred embodiments. However, it must be understood that the apparatus and method of using the apparatus may be practiced otherwise than is specifically illustrated without departing from its spirit or scope.

IV. Glossary of Element Numbers, Names, and Definitions

Table 1 below provides a chart of element numbers, names, and definitions.

| Number | Name | Definition/Description |
|---|---|---|
| 70 | Air | A mixture of gases that surrounds the earth. When loading an prior syringe with a liquid 80, air 70 within the prior art syringe is substantially displaced with liquid 80, but a significant volume of air 70 nonetheless remains within the prior art syringe. The apparatus 100 provides a way for the user 90 to easily, quickly, and comprehensively remove air 70 from an apparatus 100 that is loaded with the desired liquid 70. |
| 80 | Liquid | A substance that flows freely but is of constant volume. Common examples of liquids 80 include oils 82 and water 88. |
| 82 | Oil | A common category of liquids 80. Oils 82 are typically greasy. Oils 82 can derived from plan, animal, or mineral sources that do not dissolve in water and are often used as lubricants, fuels, and for ingestion or imbibing by human beings. |
| 84 | Water | A common category of liquids. Water is $H_2O$. |
| 90 | User | A human being interacting with the apparatus 100. Users 90 can be involved in loading the apparatus 100 with liquid 80 as well as unloading the apparatus 100 by discharging the liquid 80 out of the apparatus 100. |
| 100 | Apparatus or Syringe Assembly or Syringe | A configuration of components that can include a plunger assembly 200, a barrel 300, and a stopper assembly 400. The apparatus 100 can enable the ability of a user 90 to fill the barrel 300 with a desired liquid 80 while avoiding the trapping of air 70 or undesired liquids 80 in the barrel 300. |
| 110 | Material | A substance present in the structure of the apparatus 100. The apparatus 100 can be comprised of a variety of different materials 110. Examples of materials 110 include but are not limited to metal 120, glass 130, plastic 140, silicone 150, and rubber 160. |
| 120 | Metal | A solid material 110 that is typically hard, shiny, malleable, fusible, and ductile, with good electrical and thermal conductivity (e.g., iron, gold, silver, copper, and aluminum, and alloys such as brass and steel). |
| 130 | Glass | A hard and brittle material 110, typically transparent or translucent, made by fusing sand with soda, lime, and sometimes other ingredients and cooling rapidly. It is used to make windows, drinking containers, and other articles |
| 140 | Plastic | A synthetic material 110 made from a wide range of organic polymers such as polyethylene, PVC, nylon, etc., that can be molded into shape while soft and then set into a rigid or slightly elastic form. |
| 150 | Silicone | A class of synthetic materials 110 that are polymers with a chemical structure based on chains of alternate silicon and oxygen atoms, with organic groups attached to the silicon atoms. Such compounds are typically resistant to chemical attack and insensitive to temperature changes and are used to make rubber, plastics, polishes, and lubricants. |
| 160 | Rubber | A tough elastic polymeric substance made from the latex of a tropical plant or synthetically. |
| 200 | Plunger Assembly | A configuration of components that is used to load and unload the apparatus 100. After the user 90 or some automated mechanism loads the desired liquid 80 into the barrel 300 of the apparatus 100, the plunger assembly 200 is pressed towards the liquid 80 in the barrel 300 to remove the remaining air 70 from within the barrel 100 and to secure the liquid 80 within the apparatus 100. To unload the apparatus 100, the plunger assembly 200 is pressed further into the barrel 300 after the stopper assembly 400 has been removed from the barrel 300, allowing the liquid to be pushed outside the barrel 300 by the plunger assembly 200. In a preferred category of embodiments, the plunger assembly 200 is comprised of a plunger rod 210 and a movable tip 280. The tightening of the movable tip 280 on the plunger rod 210 enables the removal of air 70 from within the apparatus 100. The plunger assembly 200 is typically comprised of metal 120, but it can also be made of glass 130 or plastic 140. |
| 210 | Plunger Rod | A component that is pushed by the user 90 into the barrel 300. |
| 220 | Tab | The uppermost portion of the plunger rod 220. The tab 220 is typically what the user 80 directly pressed down into the barrel 300. |
| 230 | Main Body | The portion of the plunger rod 210 between the tab 220 and the connector 250. |
| 240 | Heat Source | Some embodiments of the apparatus 100 can include the functionality of heating the liquid 80 in the apparatus 100. A heat source 240, such as a batter 242, can be positioned within the plunger rod 210. |

-continued

| Number | Name | Definition/Description |
|---|---|---|
| 242 | Battery | A common example of a heat source 240 that can be embedded into the plunger rod 210. |
| 246 | Button | A user control component that can be used to activate/deactivate the heating of the liquid 80. |
| 248 | USB Port | A component that enables the charging of the batter 242. |
| 250 | Connector | A protrusion at the bottom of the plunger rod 210 onto which the movable tip 280 is secured to the plunger rod 210. |
| 252 | Threads | In many embodiments of the apparatus 100, the connector 250 will include various threads 252 on the exterior surface to facilitate the mating and separation of the movable tip 280 with respect to the plunger rod 210. Threads 252 are typically comprised of metal 120. |
| 254 | O-Ring | In many embodiments of the apparatus 100, the connector 250 will include one or more o-rings 254 on the exterior surface to facilitate the mating and separation of the movable tip 280 with respect to the plunger rod 210. 0-rings 254 are typically comprised of silicone 150, although other materials 110 such as plastic 140 or rubber 160 can also be used. |
| 280 | Movable Tip | A component that can be removably attached to the plunger rod 210. In a preferred embodiment of the apparatus 100, the movable tip 280 is loosely secured on the plunger rod 210 when the plunger rod 210 is inserted into the barrel 300. While the plunger rod 210 is within the barrel 300, the movable tip 280 is further tightened onto the connector 250 by rotating the plunger rod 210. In |
| 282 | Hole | An opening in the movable tip 280 that facilitates mating between the movable tip 280 onto the connector 250. |
| 284 | Axial Hole | A hole 282 runs through the vertical axis of the movable tip 280. The diameter of the axial hole is typically smallest in the bottom surface 290. |
| 286 | O-Ring | A ring around the outside of the movable tip 280 that facilitates the movement of the plunger assembly 200 within the barrel 300. The o-ring 286 is typically comprised of silicone 150, although other materials 110 such as plastic 140 or rubber 150 can also be used. |
| 290 | Bottom Surface | A surface on the movable tip 280 that along with the bottom most portion of the connector 250 make up the bottom-most surface on the plunger assembly 200. |
| 292 | Heating Element | A component that generates heat when power from the battery 242 is provided to the heating element 292. Heating elements 292 serve to heat the liquid 80. A heating element 292 is typically positioned near the bottom of the plunger assembly 200 unless the barrel 300 includes one or more wires 380. Heating elements 292 can be configured in the movable tip 280 of the plunger assembly 200 to activate once the movable tip 280 is secured tightly and fully on the connector 250. |
| 300 | Barrel | A container for the liquid 80 stored in the apparatus 100. The barrel 300 is typically comprised of glass 130 or plastic 140, but other materials 110 can be used. |
| 310 | Lip | A rim the circles around the mouth 320 of the barrel 300. |
| 320 | Mouth | An opening at the top of the barrel 300 into which liquid 80 is loaded into the barrel 300. |
| 330 | Cavity | An internal space within the barrel 300 into which liquid 80 is stored. |
| 340 | Main Body | The portions of the barrel 300 from just below to the lip 310 to the base 350. |
| 350 | Base | A portion of the barrel 300 where the diameter narrows. The base 350 represents the junction point between the main body 340 and the tip 360. |
| 360 | Tip | A protrusion of the barrel 300 that is positioned below the base 350. |
| 370 | Opening | A hole at the bottom of the tip 360 where the liquid 80 is discharged out of the barrel 300. |

-continued

| Number | Name | Definition/Description |
|---|---|---|
| 380 | Wire | A string of heat-conductive material, typically a metal 120, that in conjunction with the heat source 240 such as a battery 242. |
| 400 | Stopper Assembly | A configuration of components that is used to prevent liquid 80 from being discharged out of the apparatus 100 until such discharge is desired. Before the apparatus 100 is loaded with the desired liquid, the stopper assembly 400 is attached to the tip 360 of the barrel 300. Before the liquid 80 is discharged out of the barrel 300, the stopper assembly 400 is removed from the tip 360 of the barrel 300. The stopper assembly 400 can include a tip cap 410, a stopper case 450, and a stopper 490. |
| 410 | Tip Cap | A component that is capable of being secured to the bottom of the stopper assembly 400 (i.e. the tip 360) and the top of the stopper case 450. The tip cap 410 is typically made up of plastic 140, although other types of materials 110 can be used. |
| 420 | Hole | An opening in the tip cap 410 that provides for mating with the tip 360. |
| 422 | Axial Hole | A hole 420 than runs through the vertical axis of the tip cap 410. |
| 430 | Connector | A component within the tip cap 410 to facilitates the mating of the tip cap 410 to the tip 360 of the barrel 300. |
| 432 | Gripping Tooth | An example of a connector 430 that is used to secure the tip cap 410 on the tip 360 of the barrel 300. |
| 440 | Chamber | A space within the tip cap 410 into which the stopper case 450 can be removably secured into position. |
| 442 | Chamber Threads | Threads within the chamber 440 that facilitate the mating between the tip cap 410 and the stopper case 450. |
| 450 | Stopper Case | A cartridge the holds the stopper 490. In many embodiments of the apparatus 100, the stopper case 450 mates with a tip cap 410. |
| 460 | Case Tip | A portion of the stopper case 450 that provides for mating with the tip cap 410. |
| 462 | Case Tip Opening | An opening in the top of the stopper case 450. |
| 464 | Case Tip Thread | A thread that provides for securing the case tip 460 of the stopper case 450 into the tip cap 410 of the stopper assembly 400. |
| 470 | Case Base | A portion of the stopper case 450 that provides for the bottom |
| 480 | Case Chamber | The space within the stopper case 450 in which the stopper 490 is positioned. |
| 490 | Stopper | A component within the stopper case 450 that prevents the discharge of liquid 80 outside the apparatus 100 when the stopper assembly 400 is secured on the barrel 300. The stopper 490 is typically comprised of a silicone 150 or rubber 160, but other materials 110 may also be used. The geometry of the stopper 490 typically matches that of the stopper case 450. Some embodiments of the stopper 490 can include a stopper base 492, a stopper tip 492, and a stopper opening 494. |
| 492 | Stopper Base | A portion of the stopper 490 that is positioned at the bottom of the apparatus 100. |
| 494 | Stopper Tip | A portion of the stopper 494 that is positioned above the stopper base 492. The stopper tip 494 can have an opening that allows the liquid to enter a space within the stopper 490. |
| 494 | Stopper Opening | A hole in the stopper tip 494 that allows the liquid 80 to enter into the interior of the stopper 490. |
| 900 | Method | A process of using the apparatus 100 to store and subsequently discharge a liquid 800. |

V. Description of Drawings

FIG. 1A is a side view diagram illustrating an example of an apparatus 100 in an upright position that has been loaded with liquid 80, where the movable tip 280 has been tightened to the plunger rod 210. Also illustrated are examples of a barrel 300 and of a stopper assembly 400.

Figure 1B:
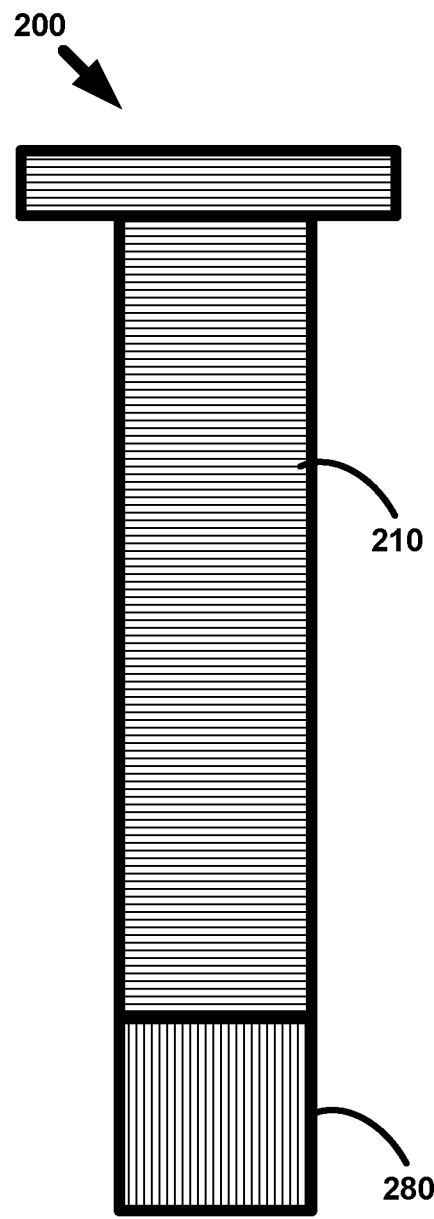
FIG. 1B is a side view diagram illustrating an example of a plunger assembly that is included in FIG. 1A.

FIG. 1B is a side view diagram illustrating an example of a plunger assembly 200 that is included in FIG. 1A. The plunger assembly 200 includes a movable tip 280 that is fully secured to the plunger rod 210.

Figure 1C:
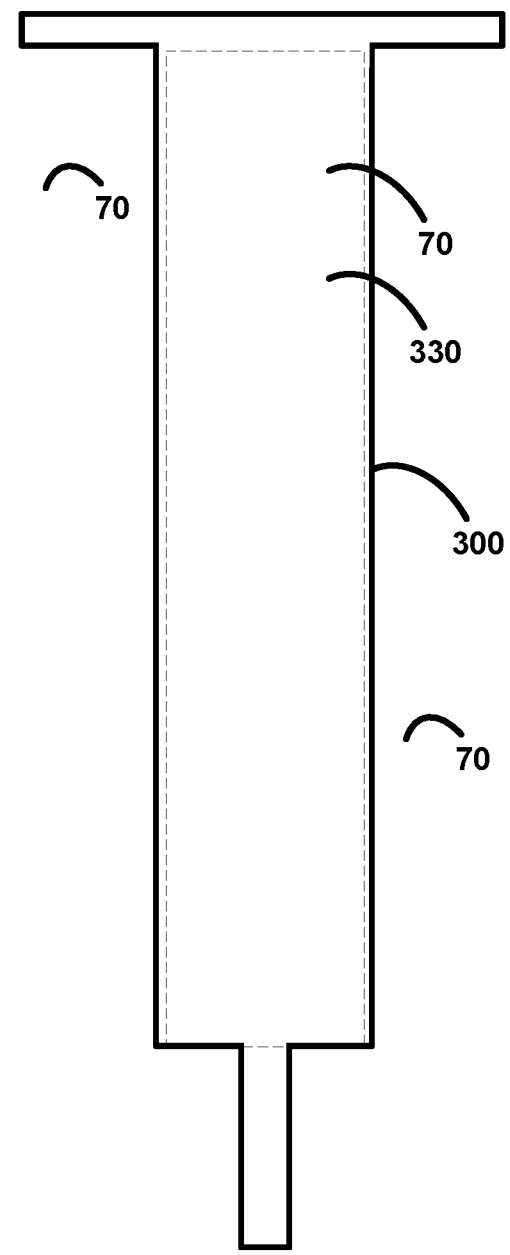
FIG. 1C is a side view diagram illustrating an example of a barrel that is included in FIG. 1A.

FIG. 1C is a side view diagram illustrating an example of a barrel 300 that is included in FIG. 1A.

Figure 1D:
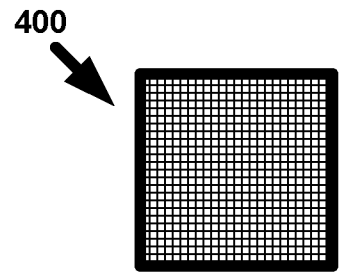
FIG. 1D is a side view diagram illustrating an example of a stopper assembly that is included in FIG. 1A.

FIG. 1D is a side view diagram illustrating an example of a stopper assembly 400 that is included in FIG. 1A.

Figures 2A, 2B, 2C:
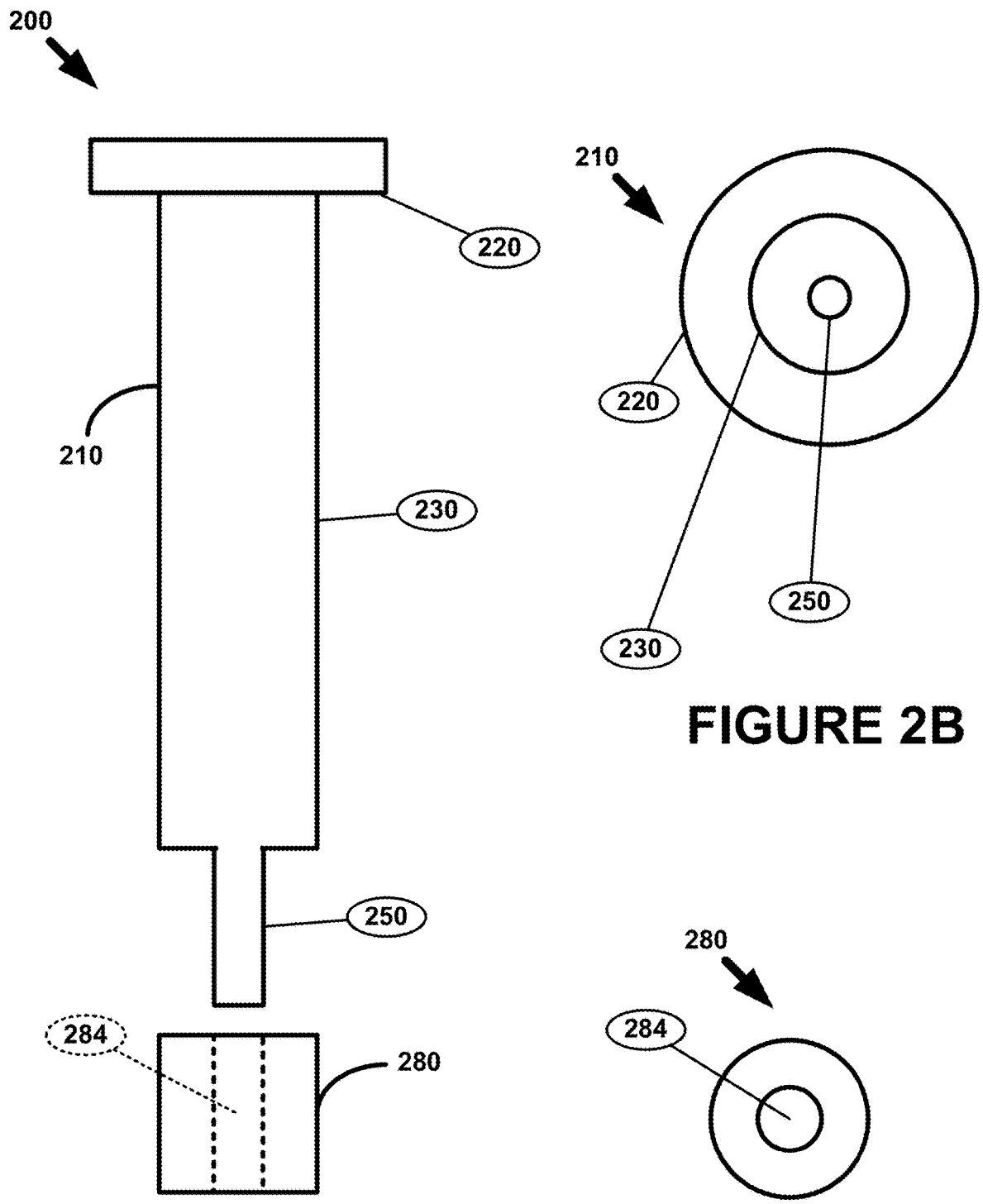
FIG. 2A is a side view diagram illustrating an example of a detached plunger assembly, where the connector of the plunger rod is totally detached from the axial hole in the movable tip.
FIG. 2B is a bottom view diagram illustrating an example of the plunger rod from FIG. 2A.
FIG. 2C is a bottom view diagram illustrating an example of the movable tip from FIG. 2A.

FIG. 2A is a side view diagram illustrating an example of a detached plunger assembly 200, where the connector 250 of the plunger rod 210 is totally detached from the axial hole 284 in the movable tip 280.

FIG. 2B is a bottom view diagram illustrating an example of the plunger rod 210 from FIG. 2A.

FIG. 2C is a bottom view diagram illustrating an example of the movable tip 280 from FIG. 2A.

FIG. 2D is a side view diagram illustrating an example of a plunger assembly 200 in an upright, attached, but not fully secured state, with the connector 250 being partially inside the axial hole 284 of the movable tip 280.

FIG. 2E is a side view diagram illustrating an example of a plunger assembly 200 in an upright, attached, and fully secured state, with the connector 250 being securely positioned through the axial hole 284 of the movable tip 280. In many embodiments, the connector 250 and/or the axial hole 284 will be threaded to facilitate secure mating between the two components.

FIG. 3A is a side view diagram illustrating an example of a barrel 300 in an upright position. Also illustrated in the figure are examples of a lip 310, a mouth 320, an internal cavity 330 for holding the liquid 80, a main body 340, a base 350, a tip 360, and an opening 370. Some embodiments of the apparatus 100 that enable the heating of the liquid 80 in the cavity 330 may include conductive wires 380 in the barrel 300 to transmit heat from the heat source 240 or heat elements 282 to the liquid 80.

FIG. 3B is a bottom view diagram illustrating an example of a barrel 300.

FIG. 4A is a side view diagram illustrating an example of a stopper assembly 400 in an upright but disassembled state. In some embodiments, the stopper assembly 400 consists solely of one integral component such as a stopper 490. In other embodiments such as the illustration in FIG. 4A, the stopper assembly 400 includes a stopper 490 housed in a stopper case 450 that mates with a tip cap 410 that is adapted to be secured over the opening 370 on the tip 360 of the barrel 300.

FIG. 4B is a top view diagram illustrating an example of a tip cap 410.

FIG. 4C is a top view diagram illustrating an example of a stopper case 450.

FIG. 4D is a top view diagram illustrating an example of a stopper 490.

Figure 4E:
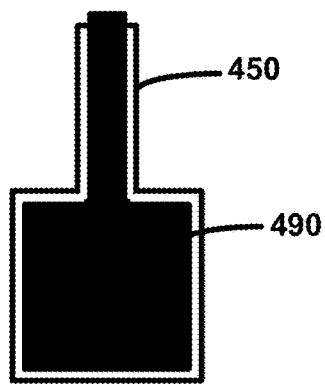
FIG. 4E is a side view diagram illustrating an example of a stopper secured within a stopper case, with both components being in an upright position.

FIG. 4E is a side view diagram illustrating an example of a stopper 490 secured within a stopper case 450, with both components being in an upright position. In some embodiments, the stopper 490 is not intended to be removable from the stopper case 450 by a user 90.

Figure 4F:
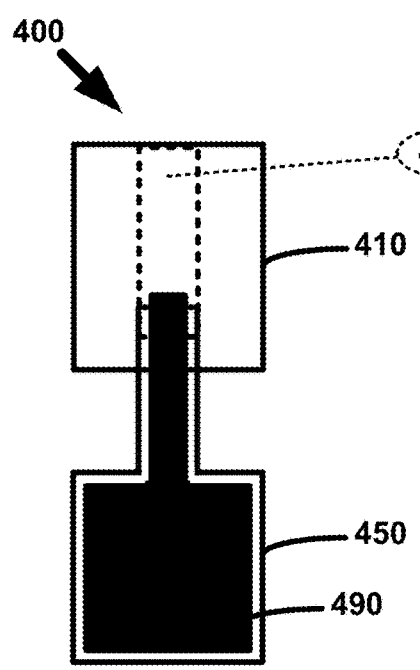
FIG. 4F is a side view diagram illustrating an example of a stopper assembly in an attached but not fully secured position.

FIG. 4F is a side view diagram illustrating an example of a stopper assembly 400 in an attached but not fully secured position. The mating between the stopper case 450 and the tip cap 410 can involve threaded surfaces, o-rings, and other connective components known in the art.

Figure 4G:
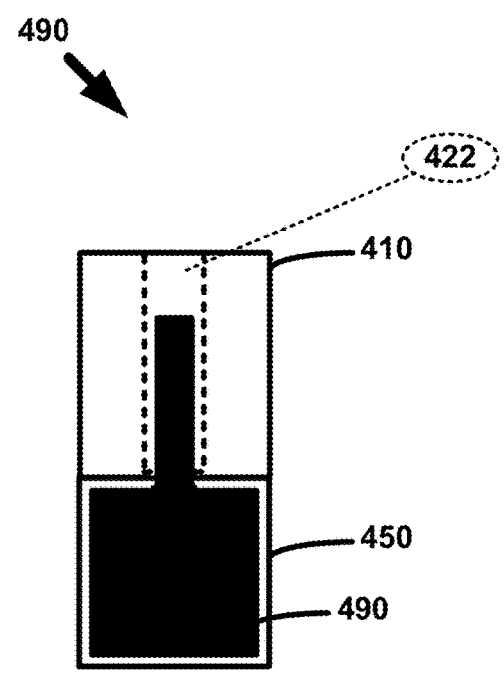
FIG. 4G is a side view diagram illustrating an example of a stopper assembly in a fully attached and secured position.

FIG. 4G is a side view diagram illustrating an example of a stopper assembly 400 in a fully attached and secured position.

FIG. 5A is a side view diagram illustrating an example of a stopper assembly 400 being attached but not fully secured to the tip 360 of a barrel 300.

FIG. 5B is a side view diagram illustrating an example of a stopper assembly 400 that is fully attached and secured to the tip 350 of a barrel 300.

Figures 5C, 5D:
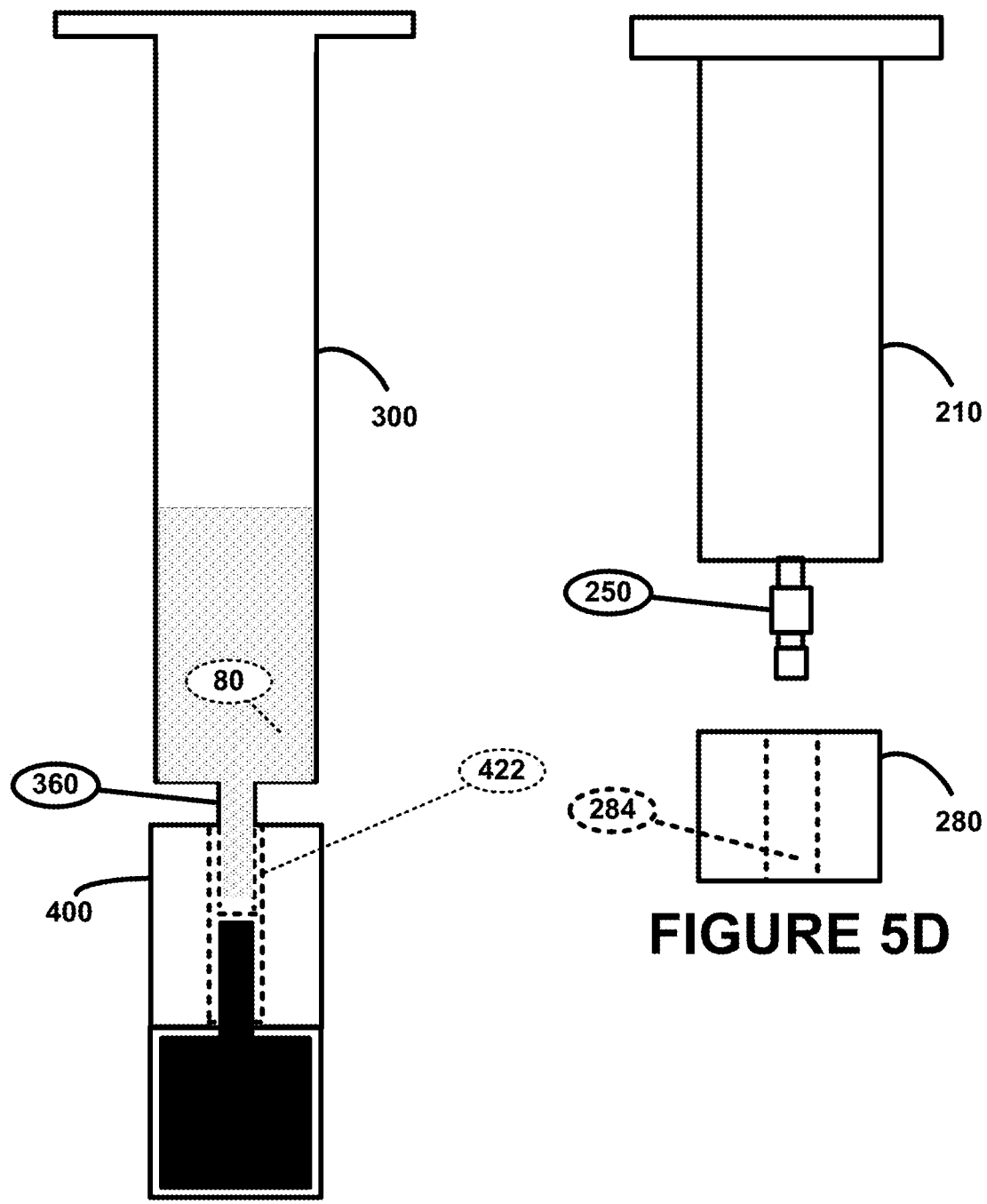
FIG. 5C is a side view diagram illustrating an example of the components in FIG. 5B, with a liquid loaded into the barrel.
FIG. 5D is a side view diagram illustrating an example of a disassembled plunger assembly that is to be assembled and used with respect to the components disclosed in FIG. 5C.

FIG. 5C is a side view diagram illustrating an example of the components in FIG. 5B, with a liquid 80 loaded into the barrel 300.

FIG. 5D is a side view diagram illustrating an example of a disassembled plunger assembly 200 that is to be assembled and used with respect to the components disclosed in FIG. 5C.

FIG. 5E is a side view diagram illustrating an example of an assembled plunger assembly 200 where the movable tip 280 is not fully tightened/secured to the plunger rod 210 while still being attached to the connector 250 on the plunger rod 210.

FIG. 5F is a side view diagram illustrating an example of the plunger assembly 200 of FIG. 5E being inserted into the barrel 300 and stopper assembly 400 of FIG. 5C. The movable tip 280 has been pushed down to the point where liquid 80 occupies the barrel 300. The movable tip 280 has still not been fully tightened with respect to the plunger rod 210.

Figure 5G:
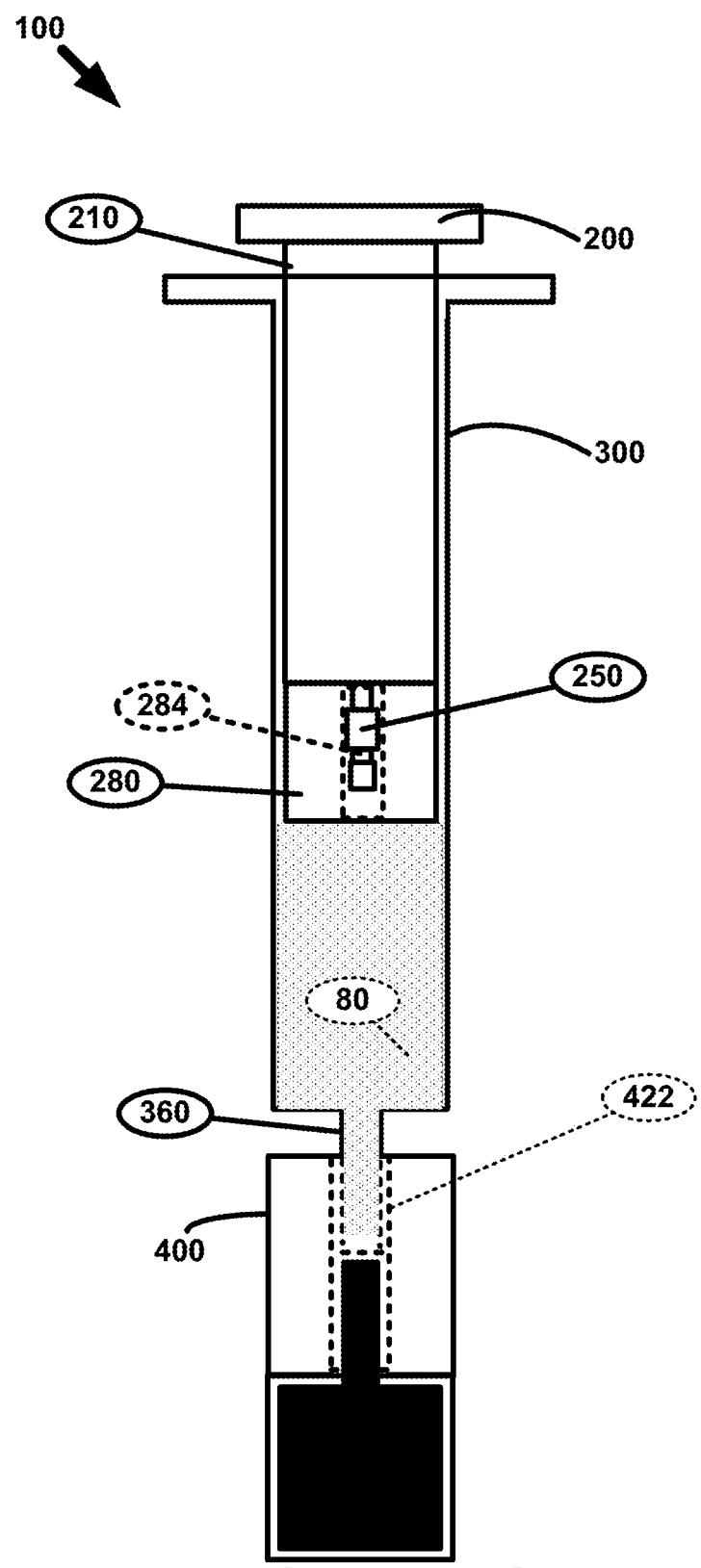
FIG. 5G is a side view diagram illustrating an example of an apparatus similar to FIG. 5F, except that the plunger rod has been fully tightened/secured to the movable tip. Doing so pushed the air in the barrel cavity out of the axial hole in the movable tip.

FIG. 5G is a side view diagram illustrating an example of an apparatus 100 similar to FIG. 5F, except that the plunger rod 210 has been fully tightened/secured to the movable tip 280. Doing so pushed the air 70 in the barrel cavity 330 out of the axial hole 284 in the movable tip 280.

FIG. 6A is a flow chart diagram illustrating an example of using the plunger assembly 200 in utilizing a syringe 100. At 930, liquid 80 is loaded into the barrel 300. At 940, the movable tip 280 is attached to the plunger rod 210, but not tightened so that air 70 can travel out the hole 282 in the movable tip 280. At 950, the plunger assembly 200 is inserted into the barrel 300 such that the bottom surface of the movable tip 280 is at "high water line" of the liquid 80. At 960, the plunger rod 210 is tightened by twisting the tab 220. The apparatus 100 is thus fully loaded, and no air 70 remains in the cavity 330 with the liquid 80.

FIG. 6B is a flow chart diagram illustrating an example of using the plunger assembly 400 in utilizing a syringe 100. Additional steps are identified at 920, 926, 946, 956, and 970.

Figure 7:
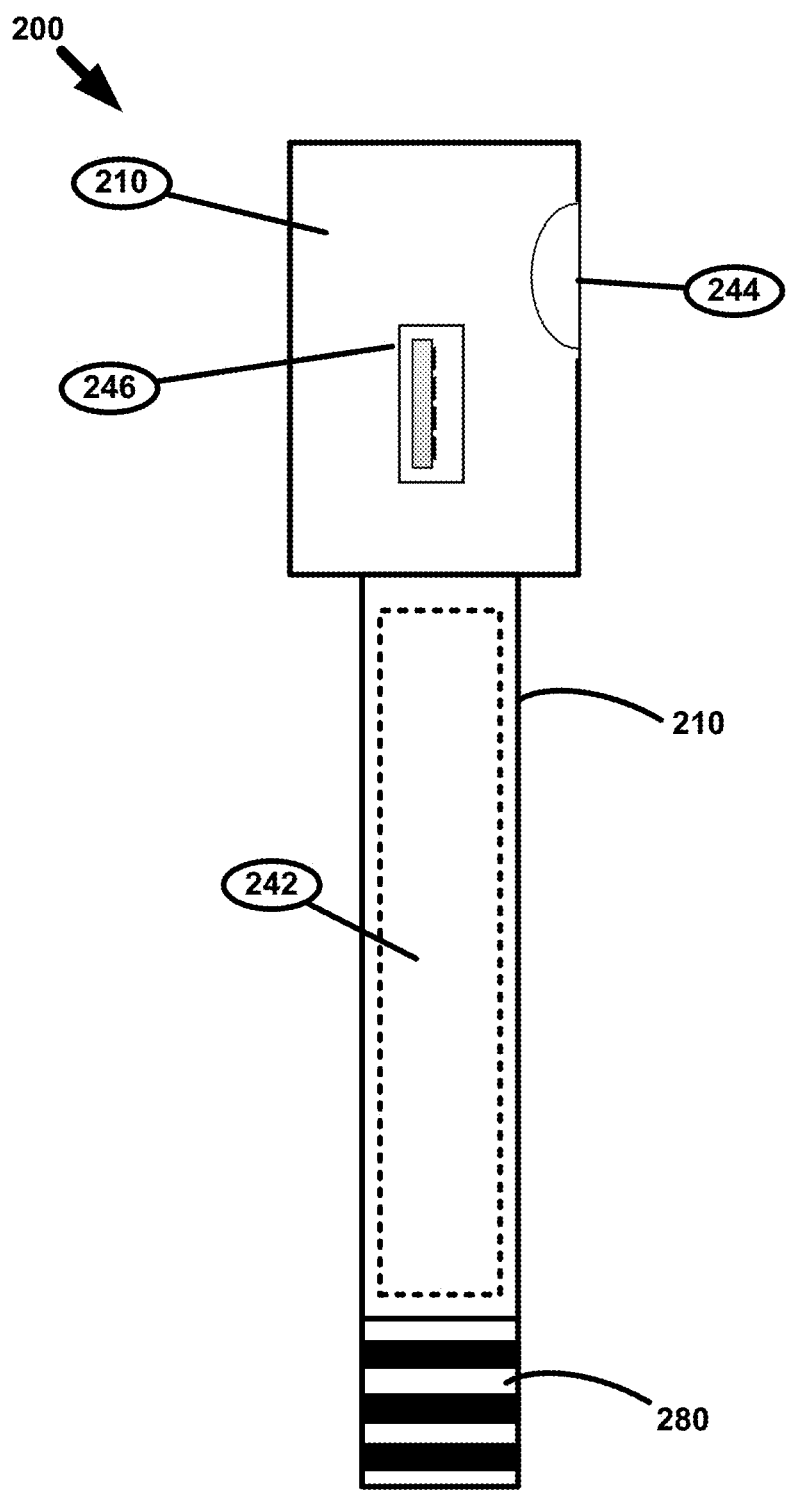
FIG. 7 is side view diagram of a plunger assembly that includes certain electrical components that can be used to heat the liquid in the apparatus.

FIG. 7 is side view diagram of a plunger assembly 200 that includes certain electrical components that can be used to heat the liquid 80 in the apparatus 100. Some but not all heated embodiments of the apparatus 100 will includes wires 380 in the barrel to facilitate the transmission and distribution of heat to the liquid 80 in the cavity 330.

Figure 8A:
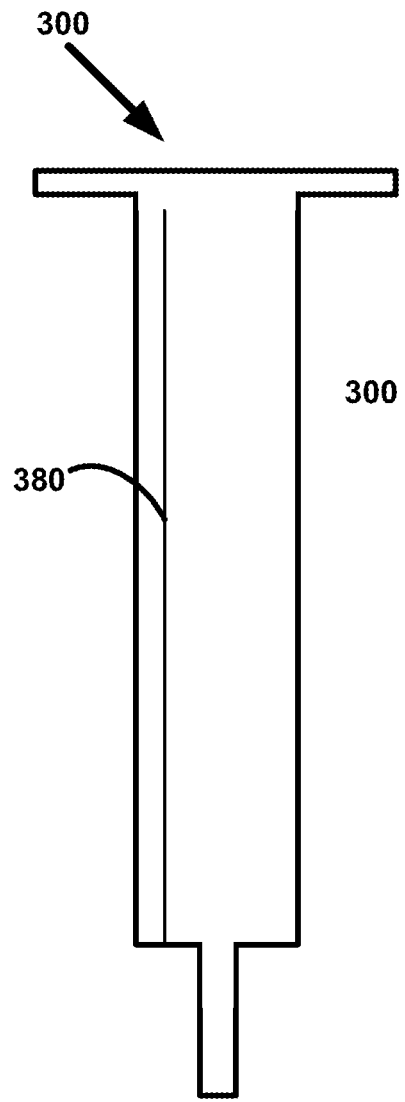
FIG. 8A is a side view diagram illustrating an example of a barrel.

FIG. 8A is a side view diagram illustrating an example of a barrel 300 that includes a wire 380.

Figure 8B:
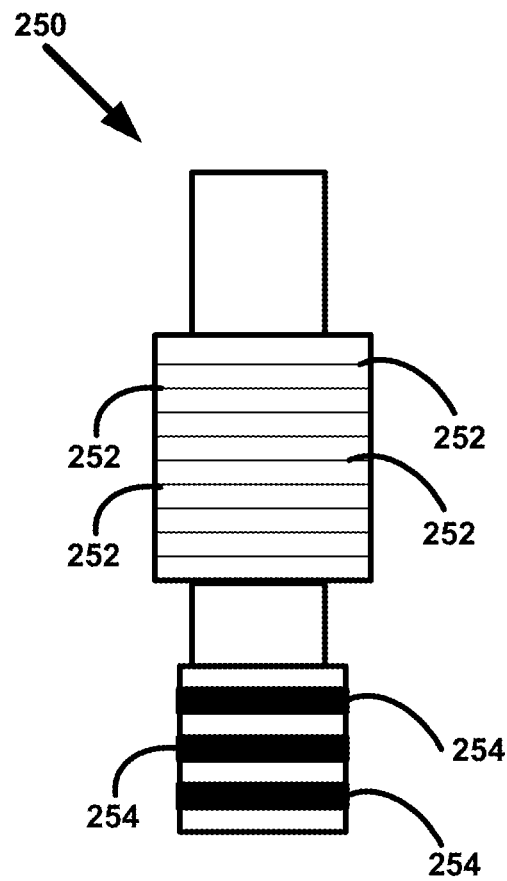
FIG. 8B is a side view diagram illustrating an example of a connector of a barrel assembly that includes o-rings and threads.

FIG. 8B is a side view diagram illustrating an example of a connector 250 of a barrel assembly 300 that includes o-rings 254 and threads 252.

Figure 8C:
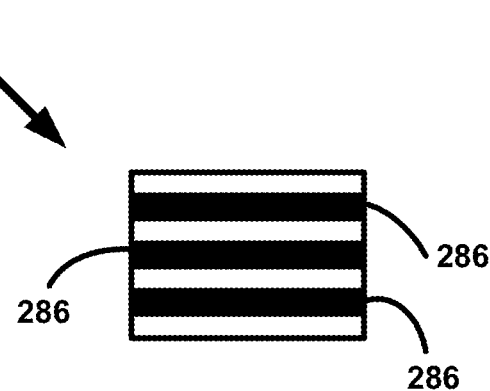
FIG. 8C is a side view diagram illustrating an example of a movable tip that includes o-rings.

FIG. 8C is a side view diagram illustrating an example of a movable tip 280 that includes o-rings 286 on the exterior surface of the movable tip 280.

Figure 8D:
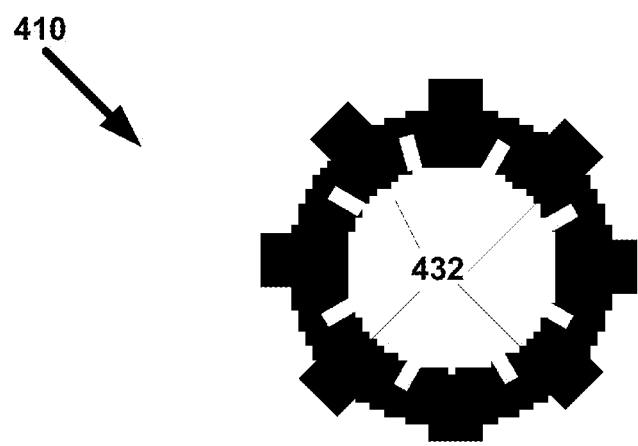
FIG. 8D is a top view diagram illustrating an example of a tip cap that includes gripping teeth.

FIG. 8D is a top view diagram illustrating an example of a tip cap 410 that includes gripping teeth 432.

The invention claimed is:

1. An apparatus (100) that provides for being loaded with a liquid (80) and subsequently discharging the liquid (80), said apparatus (100) comprising:

a barrel (300) that is adapted to hold the liquid (80);

a stopper assembly (400) removably secured at the bottom of said barrel (300) until the liquid (80) is to be discharged out of said barrel (300); and a plunger assembly (200) that is adapted to remove a plurality of air (70) from said barrel (300) after said barrel (300) is loaded with the liquid (80);

said plunger assembly (200) including a plunger rod (210) and a movable tip (280) that is removably secured to said plunger rod (210) rotating said plunger rod (210) while said movable tip (280) is inserted inside said barrel (300);

wherein said plunger assembly (200) includes a battery (242) that is embedded in said plunger rod (210), wherein said battery (242) is adapted to heat the liquid (80), and wherein said apparatus (100) includes only one barrel (300);

wherein said plunger rod (210) includes a connector (250) that is adapted to be removably fixed to said movable tip (280), and wherein said movable tip (280) is adapted to move relative to said connector (250) while said movable tip (250) is within said barrel (300);

said connector (250) comprising a plurality of threads (252) and a plurality of o-rings (254) that are adapted to mate with said movable tip (280);

wherein said movable tip (280) is adapted to become attached to said connector (250) even though said movable tip (280) is not attached to said connector (250) when said movable tip (280) is placed into said barrel (300).

2. The apparatus (100) of claim 1, said stopper assembly (400) including a tip cap (410) that is adapted to be removably secured to a tip (360) on said barrel (300).

3. The apparatus (100) of claim 2, said stopper assembly (400) including a stopper (490) secured within a stopper case (450), said stopper case (450) being adapted to be removably secured to said tip cap (410).

4. The apparatus (100) of claim 3, wherein said stopper (490) is comprised of a silicone (140).

5. The apparatus (100) of claim 3, wherein said tip cap (410) includes a plurality of gripping teeth (432) adapted to secure said tip (360) within an axial hole (422) while said barrel (300) holds the liquid (80).

6. The apparatus (100) of claim 5, wherein said tip cap (410) further includes a chamber (440) with a plurality of chamber threads (442), wherein said stopper case (450) includes a case tip (460) adapted to be removably secured within said chamber (440).

7. A plunger assembly (200) adapted for insertion into an apparatus (100) that includes a barrel (300) with a cavity (330) for holding a liquid (80) and a stopper assembly (400) that prevents the liquid (80) from flowing out of a tip (360) in the barrel (300), said plunger assembly (200) comprising:

a plunger rod (210) that is adapted to be inserted into the barrel (300); and a movable tip (280) that is adapted to removably secured to said plunger rod (210) while said movable tip (280) is positioned within the barrel (300);

wherein said plunger assembly (300) includes a battery (242) that is embedded in said plunger rod (210), wherein said battery (242) is adapted to heat the liquid (80), and wherein said apparatus (100) includes only one barrel (300);

wherein said plunger rod (210) includes a battery (242), and wherein said battery (242) is adapted to heat said wire (380), warming the liquid (80) within the barrel (300).

8. A method (900) for storing a liquid (80) with a syringe assembly (100) that includes a stopper assembly (400) and a plunger assembly (200) which comprises a movable tip (280) and a plunging rod (210), said method (900) comprising:

loading (930) a liquid (80) into a barrel (300) of the syringe assembly (100);

attaching (940) said movable tip (280) to said plunging rod (210);

inserting (950) said movable tip (280) into said barrel (300); and tightening (960) said movable tip (280) relative to said plunging rod (210), wherein a plurality of air (70) in the barrel (300) is pushed out of said barrel (300) through an axial hole (284) in said movable tip (280);

wherein said plunger rod (210) includes a battery (242) that is embedded in said plunger rod (210), wherein said battery (242) is adapted to heat the liquid (80), and wherein said syringe assembly (100) includes only one barrel (300).

9. The method (900) of claim 8, said method (900) further comprising:

heating (970) the liquid (80) in said barrel (300) by sending electricity from a battery (242) in said plunging rod (210).

10. The method (900) of claim 8, said method (900) further comprising:

positioning (956) a bottom surface (290) of said movable tip (280) at a highest position within said barrel (300) that is occupied by the liquid (80).

11. The method (900) of claim 8, said method (900) further comprising:

securing (920) a stopper case (450) that includes a stopper (490) to a tip cap (410) that includes an axial hole (422); and attaching (926) said tip cap (410) to a tip (360) of said barrel (300).

12. The method (900) of claim 11, said method (900) wherein attaching (940) said movable tip (280) to said plunging rod (210) includes (946) twisting a connector (250) at the bottom of said plunger rod (210) into said axial hole (284) in said movable tip (280), wherein said connector (250) includes a plurality of threads (252) and a plurality of O-rings (254) to facilitate a removably secure attachment between said plunging rod (210) and said movable tip (280).

* * * * *